United States Patent
Chen et al.

(10) Patent No.: US 9,945,849 B2
(45) Date of Patent: Apr. 17, 2018

(54) METHODS FOR PRODUCING SURFACES THAT RESIST NON-SPECIFIC PROTEIN BINDING AND CELL ATTACHMENT

(71) Applicant: Corning Incorporated, Corning, NY (US)

(72) Inventors: Xiaoxi (Kevin) Chen, Natick, MA (US); William Galbraith, Windham, NH (US)

(73) Assignee: Corning Incorporated, Corning, NY (US)

( * ) Notice: Subject to any disclaimer, the term of this patent is extended or adjusted under 35 U.S.C. 154(b) by 175 days.

(21) Appl. No.: 14/178,875

(22) Filed: Feb. 12, 2014

(65) Prior Publication Data

US 2014/0162078 A1    Jun. 12, 2014

Related U.S. Application Data

(63) Continuation of application No. 13/927,820, filed on Jun. 26, 2013, now Pat. No. 8,652,584, which is a
(Continued)

(51) Int. Cl.
*G01N 33/543*  (2006.01)
*B05D 3/14*  (2006.01)

(52) U.S. Cl.
CPC ......... *G01N 33/54393* (2013.01); *B05D 3/14* (2013.01); *Y10T 428/31* (2015.01);
(Continued)

(58) Field of Classification Search
CPC ............................ G01N 33/54393; B05D 3/14
(Continued)

(56) References Cited

U.S. PATENT DOCUMENTS 3,810,468 A    5/1974 Harper et al.
5,080,924 A    1/1992 Kamel et al.
(Continued)

FOREIGN PATENT DOCUMENTS

JP    08173144 A    7/1996
JP    11315157 A    11/1999
(Continued)

OTHER PUBLICATIONS

Tiziani (carbohydrate Research 338 (2003) 1083-1095).*
(Continued)

*Primary Examiner* — Joel G Horning
(74) *Attorney, Agent, or Firm* — Susan S. Wilks

(57) ABSTRACT

A method is disclosed herein for treating a polymeric surface to resist non-specific binding of biomolecules and attachment of cells. The method includes the steps of: imparting a charge to the polymeric surface to produce a charged surface; exposing the charged surface to a nitrogen-rich polymer to form a polymerized surface; exposing the polymerized surface to an oxidized polysaccharide to form an aldehyde surface; and exposing the aldehyde surface to a reducing agent. Advantageously, a method is provided which produces surfaces that resist non-specific protein binding and cell attachment and that avoids the use of photochemical reactions or prior art specially designed compounds.

19 Claims, 2 Drawing Sheets

Related U.S. Application Data continuation of application No. 11/496,933, filed on Jul. 31, 2006, now Pat. No. 8,475,886.

(60) Provisional application No. 60/705,908, filed on Aug. 5, 2005.

(52) U.S. Cl.
CPC .................. *Y10T 428/31862* (2015.04); *Y10T 428/31942* (2015.04)

(58) Field of Classification Search
USPC .......................................... 427/536; 428/524
See application file for complete search history.

(56) References Cited

U.S. PATENT DOCUMENTS

| | | | |
|---|---|---|---|
| 5,132,108 | A | 7/1992 | Narayanan et al. |
| 6,306,176 | B1 | 10/2001 | Whitbourne |
| 6,800,331 | B2 | 10/2004 | Bilyk et al. |
| 6,830,784 | B2 | 12/2004 | Gutowski et al. |
| 8,652,584 | B2 | 2/2014 | Chen et al. |
| 2002/0128234 | A1 | 9/2002 | Hubbell et al. |
| 2003/0113478 | A1 | 6/2003 | Dang et al. |
| 2003/0232198 | A1 | 12/2003 | Lamberti et al. |
| 2005/0153429 | A1 | 7/2005 | Liebmann-Vinson et al. |

FOREIGN PATENT DOCUMENTS

| | | |
|---|---|---|
| WO | 96/24392 A1 | 8/1996 |
| WO | 00/65352 A1 | 11/2000 |

OTHER PUBLICATIONS

Kim (Biomacromolecules (2000) 1, 488-492).*
Osterberg, et al., Protein-rejecting ability of surface-bound dextran in end-on and side-on configurations; Comparison to PEG, Journal of Biomedical Materials Research, 1995, pp. 741-747, vol. 29.

* cited by examiner

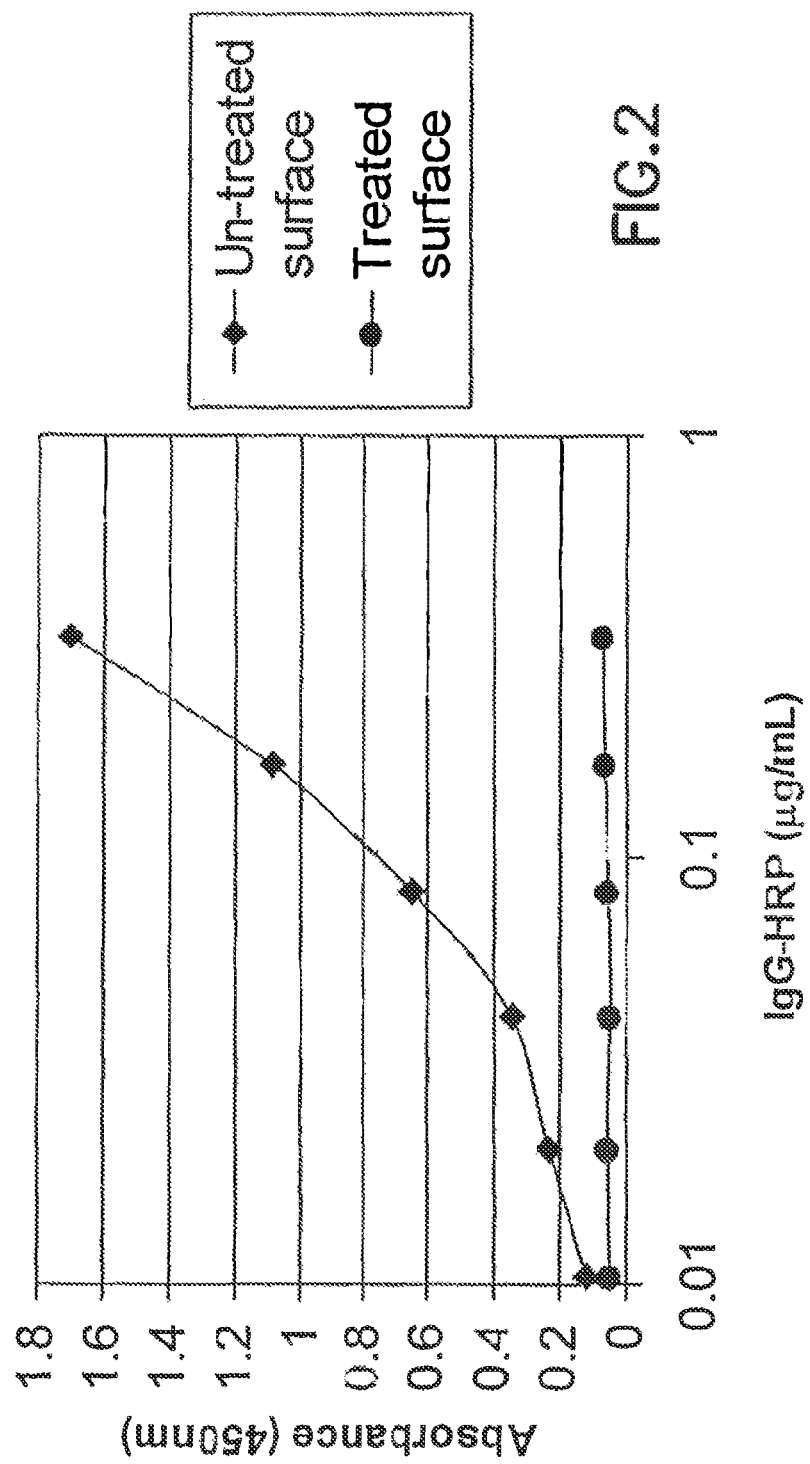

METHODS FOR PRODUCING SURFACES THAT RESIST NON-SPECIFIC PROTEIN BINDING AND CELL ATTACHMENT

CROSS-REFERENCES TO RELATED APPLICATIONS

This application is a continuation of U.S. patent application Ser. No. 13/927,820, filed Jun. 26, 2013, now U.S. Pat. No. 8,652,584, which is a continuation of U.S. patent application Ser. No. 11/496,933, filed Jul. 31, 2006, now U.S. Pat. No. 8,475,886, and claims the benefit of U.S. Provisional Patent Application No. 60/705,908, filed Aug. 5, 2005, the entire contents of which are incorporated by reference herein.

FIELD OF THE INVENTION

The present invention relates to methods of treating plastic surfaces which resist non-specific protein binding or cell attachment, and surfaces prepared by same.

BACKGROUND OF THE INVENTION

Bare plastic surfaces, such as polystyrene surfaces, typically do not resist non-specific protein binding or cell attachment. Surfaces modified with a dense and stable layer of polymers such as polyethylene glycol or hydrogels, such as dextran, are known to resist non-specific protein binding and cell attachment. In the prior art, in order to create a dense and stable layer of protective polymers or hydrogels on a plastic surface, the plastic surface was typically treated with a photochemical reaction to activate the surface or with prior art specially designed chemicals that have a high affinity to the relevant surface.

SUMMARY OF THE INVENTION

A method is disclosed herein for treating a polymeric surface to resist non-specific binding of biomolecules and attachment of cells. The method includes the steps of: imparting a charge to the polymeric surface to produce a charged surface; exposing the charged surface to a nitrogen-rich polymer to form a polymerized surface; exposing the polymerized surface to an oxidized polysaccharide to form an aldehyde surface; and exposing the aldehyde surface to a reducing agent. Advantageously, a method is provided which produces surfaces that resist non-specific protein binding and cell attachment and that avoids the use of photochemical reactions or prior art specially designed compounds.

These and other features of the invention will be better understood through a study of the following detailed description and accompanying drawings.

BRIEF DESCRIPTION OF THE FIGURES

FIG. 2 is a chart comparing the non-specific binding of Immunoglobin G (IgG) on two different surfaces: one surface is untreated and the other surface was treated by the subject invention. The amount of IgG bound on the surface was detected by the amount of IgG-HRP (horseradish peroxide) conjugate it could bind, and the amount of IgG-HRP conjugate was quantified by the HRP catalyzed oxidation of TMB (3,3', 5,5' tetramethylbenzidine), which changes color upon oxidation.

DETAILED DESCRIPTION OF THE INVENTION

Figure 1:
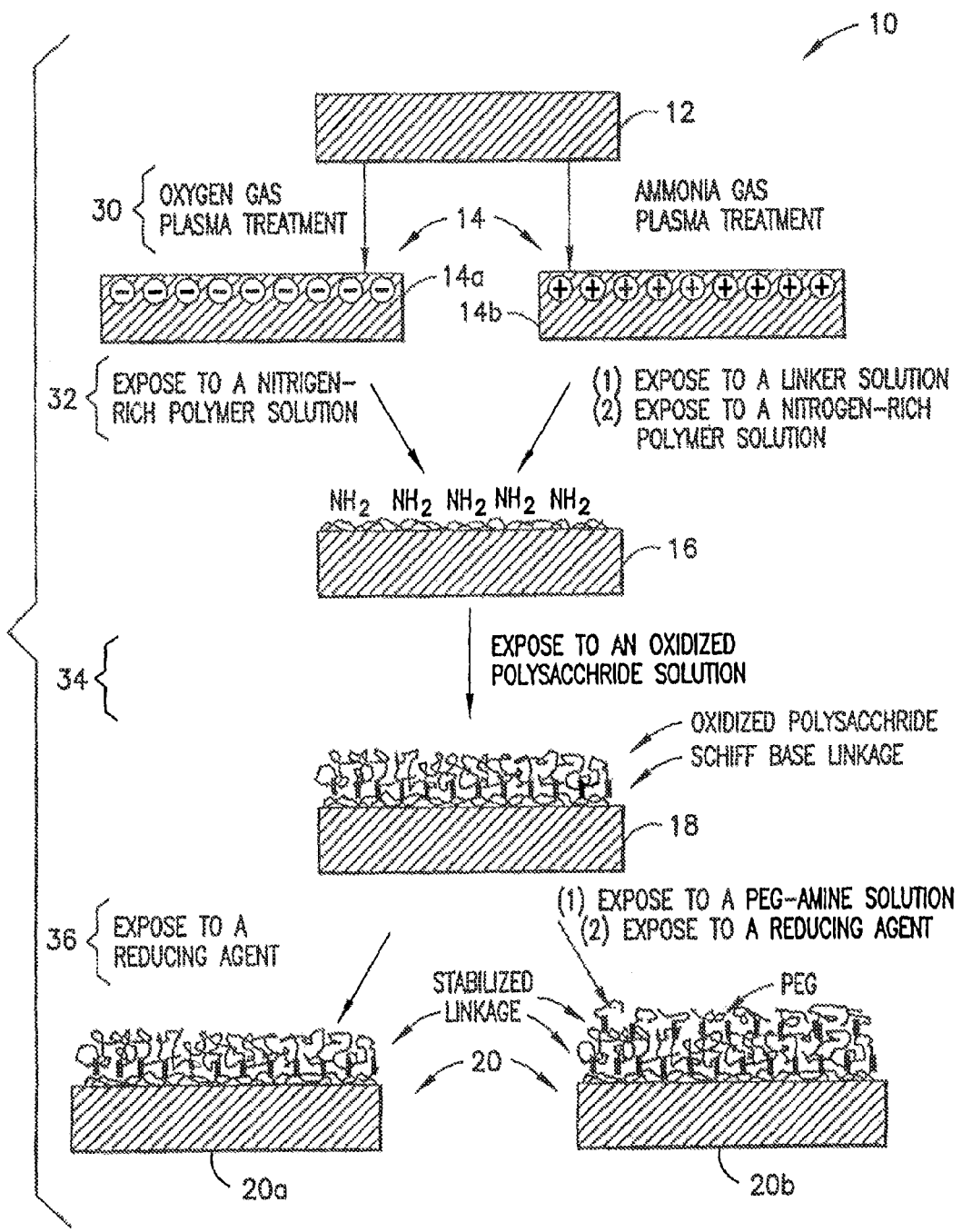
FIG. 1 is a flowchart representing a method in accordance with the subject invention.

With reference to FIG. 1, a method 10 is depicted of treating a polymeric surface 12 to resist non-specific binding of biomolecules and attachment of cells.

In an initial step 30, a charge is provided to the polymeric surface 12 of a vessel or receptacle to produce a charged surface 14. The vessel may be of any known configuration, such as a test tube, vial, flask, etc. Preferably, the polymeric surface 12 is the surface of a multiwell plate. More preferably, the polymeric surface 12 is a surface of a well of a multiwell plate. It is further preferred that the multiwell plate conform to conventional multiwell plate standards (e.g., the Standards of the Society of Biomolecular Screening) so as to be usable in drug assay handling equipment (e.g., high throughput screening (HTS) equipment).

The term "polymeric surface" as used herein refers to any suitable such polymeric surface known to those skilled in the art. Suitable examples of polymeric surfaces include those obtained from polymeric hydrocarbons. As used herein, the term "polymeric hydrocarbon" is intended to refer to those polymers and copolymers obtained from repeating monomer units which are composed of carbon and hydrogen. The polymeric hydrocarbons may be saturated or unsaturated, and substituted or unsubstituted. Substituents may include atoms other than hydrogen and carbon, as long as they are present in an amount that does not detract from the substantially hydrocarbon nature of the polymer. Such substituents include acetal, halo, hydroxy, cyano, alkoxy, amino, amido, carbamoyl, and carbamido groups. Typical examples of a polymeric hydrocarbon surface include those made from substituted and unsubstituted polyethylene, polypropylene, polystyrene, ABS, PVC, polytetrafluoroethylene, polyvinylidene, and mixtures thereof. In a preferred embodiment, the polymeric hydrocarbon surface is polystyrene.

The term "polymeric surface" is also intended to include surfaces obtained from those polymers containing one or more heteroatoms such as oxygen, nitrogen, or sulfur, in addition to carbon and hydrogen. Typical examples of such polymeric surfaces include surfaces obtained from substituted and unsubstituted polyethers, polyesters, polyamides, polyamines, polyimines, polyurethanes, polyureas, polyacetals, polycarbonates, polyacrylates, polysulfides, polysulfones, and polysulfides.

Also contemplated as being within the scope of the present invention are surfaces obtained from polymers with backbones composed significantly of heteroatoms, such as silicones.

Any known technique can be used to impart the charge to the polymeric surface 12 to produce the charged surface 14. Preferably, plasma treatment or corona discharge treatment may be utilized. With this process, a charge is imparted to the polymeric surface 12 by disposing the polymeric surface 12 into a substantially gas-free chamber, introducing a gas into the chamber, and exciting the gas. As a result, plasma is formed and applied to the polymeric surface 12 to produce the charged surface 14. A high-frequency generator may be used to ionize the gas into a plasma. In addition, the plasma may be generated using conventional plasma conditions such AC or DC power levels up to about 200 watts, radiofrequency (RF) excitation of about 0.1 to about 50 megahertz, for a durations of about 0.1 to about 30 minutes, with a gas pressure of about 0.1 to about 3.0 Torr. A conventional plasma chamber may be used, although it is preferred that the chamber be evacuated during use.

Although an RF excited plasma is preferred, any other method of generating a gas plasma may be used, for example a glow discharge or a corona discharge. For example, microwave frequencies may be employed instead of, or in addition to, RF excitation.

Gases typically used with plasma treatment and introduced into the plasma chamber include Ar, He, Ne, He, He/$H_2$, $O_2$, $N_2$, $NH_3$, and $CF_4$. In one embodiment of the invention, the charged surface 14 may be negatively charged. A negatively charged surface is specifically designated with reference numeral 14($a$) in FIG. 1. Preferably, oxygen gas is used in the plasma treatment process to produce the negatively charged surface 14($a$).

Alternatively, in another embodiment, the charged surface 14 may be positively charged. A positively charged surface is specifically designated with reference numeral 14($b$) in FIG. 1. Preferably, ammonia gas is used in the plasma treatment process to produce the positively charged surface 14($b$). Specifically, subjecting the polymeric surface 12 to ammonia gas plasma treatment creates a number of nitrogen containing, positively charged functional groups on the surface, providing the positively charged surface 14($b$).

In a next step 32 of the method 10, the charged surface 14 is exposed to a nitrogen-rich polymer to form a polymerized surface 16. The negatively charged surface 14($a$) may be exposed to the nitrogen-rich polymer without any intervening steps. However, before the positively charged surface 14($b$) may be exposed to the nitrogen-rich polymer, the positively charged surface 14($b$) is preferably first exposed to one or more suitable linkers. A variety of linkers, commonly referred to as "cross-linkers" may be used. Suitable linkers include: dialdehydes, diesters, diimidoesters, NHS-esters, hydrazides, carbodiimides, and aryl azides. Also contemplated as being within the scope of the invention are heterobifunctional linkers, i.e. those which have different functional groups on each end. For example, a suitable heterobifunctional linker would be one having an ester on one end and an aldehyde on the other end. In a preferred embodiment, the linker is a dialdehyde having the structure:

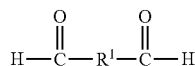

wherein $R^1$ is a $C_2$ to $C_{30}$ alkylenyl. In a more preferred embodiment, the dialdehyde is glutaraldehyde.

Preferably, the positively-charged surface 14($b$) is exposed to a solution of the linkers. Any suitable solvent or suitable mixture of solvents known to those skilled in the art may be used with the linkers. Suitable solvents include water, buffers, methanol, ethanol, isopropanol, and dimethylsulfoxide (DMSO).

Once readied, the charged surface 14 is exposed to a nitrogen-rich polymer to form the polymerized surface 16. The term "nitrogen-rich" is intended to refer to polymers bearing pendant amino groups such as $N(R^2)_2$ and $=NR^2$, wherein each $R^2$ is independently H or $C_1$ to $C_{10}$ alkyl. As used herein, the term "alkyl" intended to refer to branched and straight-chained saturated aliphatic hydrocarbon radicals having the indicated number of carbon atoms. Alkyl groups may be unsubstituted, or substituted. Suitable substituents include $C_{1-5}$ alkyl, amino, amido, cyano, carbamoyl, phenyl, heteroaryl, halogen, $C_{1-5}$alkoxy, $C_{1-5}$alkyl-C(O) H, $CO_2$H, and $CO_2$-$C_{1-5}$ alkyl. The term "alkylenyl" is intended to encompass diradical variations of alkyl groups.

Preferably, the nitrogen-rich polymer is a polyalkylenimine such as polyethylenimine. Another class of nitrogen-rich polymers suitable for the present invention is polymeric amino acids. The term "polymeric amino acid" is intended to refer to a string of repeating amino acids. Accordingly, any suitable peptide may be used as a nitrogen-rich polymer. The string of amino acids may contain a string of identical amino acids or a string of different amino acids, and in either case may be natural or man-made. Nitrogen-rich polymers based on amino acids such as lysine and arginine possess sufficient nitrogen character so as to be good examples of suitable nitrogen-rich polymers. A synthetic polymeric amino acid particularly useful in the present invention as a polymeric amino acid is poly-lysine. In a more preferred embodiment, the synthetic polymeric amino acid is poly-d-lysine.

Typically, the charged surface 14 will be exposed to a solution of the nitrogen-rich polymer, forming the polymerized surface 16. Any suitable solvent or suitable mixture of solvents known to those skilled in the art may be used. Suitable solvents include water, buffers, methanol, ethanol, isopropanol, and dimethylsulfoxide (DMSO).

In the next step 34, the polymerized surface 16 is exposed to an aldehyde-bearing polymer, thereby providing aldehyde surface 18. Any polymer bearing pendant hydroxyalkyl groups can serve as the aldehyde-bearing polymer. Preferably, the alcohols on such a polymer are oxidized to aldehydes, with the aldehydes being receptive to coupling with both the nitrogens of the polymerized surface 16 and the nitrogens of an outer layer discussed below. However, because the aldehyde surface 18 must be biologically benign, it is preferred that the alcohol-bearing polymer not be toxic to biological or cell cultures. Preferably, the aldehyde-bearing polymer is an oxidized polysaccharide in which the pendant alcohol groups have been converted to aldehyde groups. Suitable oxidized polysaccharides include oxidized polysaccharides such as oxidized amylose, oxidized amylopectin, oxidized cellulose, oxidized chitin, oxidized guaran, oxidized glucomannan, and oxidized dextran. Among these, oxidized dextran is particularly preferred. In a preferred method, the polysaccharides are oxidized by adding sodium m-periodate ($NaIO_4$) to the polysaccharide solution, with the resulting solution being incubated at room temperature in the dark for 4 hours, followed by removal of the sodium m-periodate (e.g., by dialysis).

Typically, the polymerized surface 16 will be exposed to a solution of the aldehyde-bearing polymer to form the aldehyde surface 18. Any suitable solvent or suitable mixture of solvents known to those skilled in the art may be used. Suitable solvents include water, buffers, methanol, ethanol and isopropanol.

The aldehyde surface 18 is further treated, as shown in step 36, which may involve one step or two sub-steps, in forming a stabilized surface 20.

In one embodiment, the polymerized surface 18 may be exposed to a reducing agent, thereby producing the stabilized surface 20, specifically designated for this embodiment as stabilized surface 20($a$) in FIG. 1. Preferably, the reducing agent is a boron-based reducing agent such as $NaBH_4$ or $NaCNBH_3$.

Alternatively, in another embodiment, the polymerized surface 18 is first exposed to an amine-terminated polymer. Preferably the amine-terminated polymer is an amine-terminated hydrocarbyl polymer or an amine-terminated polyether. The term "hydrocarbyl polymer" is intended to be synonymous with the term "polymeric hydrocarbon" as discussed hereinabove. In a more preferred embodiment, the amine-terminated polyether is amine-terminated polyethylene glycol. Typically, the amine-terminated polymer will be dissolved in suitable solvent when exposed to polymerized surface 18. Any suitable solvent or suitable mixture of solvents known to those skilled in the art may be used. Suitable solvents include water, buffers, methanol, ethanol and isopropanol.

Reaction of the aldehyde surface 18 and the amine groups of the amine-terminated polymer forms a reversible Schiff base linkage which can then be stabilized with a suitable reducing agent, thereby producing stabilized surface 20, specifically designated for this embodiment as stabilized surface 20(b) in FIG. 1. The suitable reducing agent is as described above with respect to the stabilized surface 20(a).

EXAMPLES

Example A

A polystyrene surface is exposed to oxygen gas plasma treatment, creating a negatively charged surface. The negatively charged surface is exposed to a solution of 1% polyethylenimine for 2 hours. The polyethylenimine coated surface is exposed to a solution of 10 mg/mL oxidized dextran for two hours. The dextran coated surface is exposed to a solution of amine-terminate polyethylene glycol for 1 hour. The polyethylene glycol surface is exposed to a solution of 1 mg/mL sodium borohydride for 1 hour.

Example B

A polystyrene surface is exposed to ammonia gas to create a positively charged surface. The positively charged surface is exposed to a solution of 10% glutaraldehyde for 1 hour. The glutaraldehyde activated surface is exposed to a solution of 1% polyethylenimine for 2 hours. The polyethylenimine coated surface is exposed to a solution of 10 mg/mL oxidized dextran for 2 hours. The dextran coated surface is exposed to a solution of 1 mg/mL amine-terminated polyethylene glycol for 1 hour. The polyethylene glycol coated surface is exposed to a solution of 1 mg/mL sodium borohydride for 1 hour.

As will be appreciated by those skilled in the art, the subject invention provides polymeric surfaces which will resist non-specific binding of biomolecules and attachment of cells. The stabilized surface 20 provides such resistance. With reference to FIG. 2, data is presented relating to the non-specific binding of IgG on two different surfaces: surfaces not treated by the method of the subject invention and surfaces which have been treated by the subject invention. In this demonstration, a 96-well polystyrene plate was treated using the method of Example A. Another 96-well polystyrene plate was not treated and was used as a reference. The surfaces in the wells of both of the plates were brought into contact with 5 µg/mL of anti-mouse IgG for 2 hours followed by washing with PBS (phosphate buffered saline). Then the surfaces were brought into contact with mouse IgG-HRP (horseradish peroxidase) conjugate (concentration ranges from 0.01 µg/mL to 0.33 µg/mL) for 1 hour followed by washing with PBS. Thereafter, the surfaces were brought into contact with TMB (3,3', 5,5' tetramethylbenzidne) solution for 8 minutes followed by adding 2N HCl to stop the reaction. The amount of anti-mouse IgG and the associated mouse IgG-HRP conjugate bound on the surfaces was quantified by the intensity of the color (detected at 450 nm) produced by the oxidized TMB. As can be seen in FIG. 2, negligible amounts of Immunoglobin G were absorbed by the treated surfaces.

Experiments have been conducted relating to the attachment of various types of adherent cells on two different surfaces: surfaces not treated by the method of the subject invention and surfaces which have been treated by the subject invention. In the following described experiments, a 6-well polystyrene plate was treated using the method of Example A. Another 6-well polystyrene plate was untreated and used as a reference.

In a first experiment, HT-1080 (human fibrosarcoma cell line) cells were cultured on both untreated and treated surfaces of 6-well plates under the same culture condition (incubation at 37° C. in growth media). Cell attachment and spreading on the surfaces were analyzed and microscopic images were taken following several days of cell culture. The HT-1080 cells attached to the untreated surface and spread on the surface as expected. However, the HT-1080 cells remained un-attached to the treated surface and formed cell aggregates floating in the media. The treated surface remained free of cells after removing the media, demonstrating the ability of the treated surface for resisting HT-1080 cell attachment.

In a second experiment, mouse embryo fibroblasts (NIH/3T3) were cultured on both untreated and treated surfaces of 6-well plates under the same culture condition (incubation at 37° C. in growth media). Cell attachment and spreading on the surfaces were analyzed and microscopic images were taken following several days of cell culture. The fibroblasts attached to the untreated surface and formed a monolayer on the surface as expected. However, the fibroblasts remained un-attached to the treated surface and formed cell aggregates floating in the media. The treated surface remained free of cells after removing the media, demonstrating the ability of the treated surface for resisting fibroblast attachment.

In a third experiment, canine chondrocytes were cultured on both untreated and treated surfaces of 6-well plates under the same culture condition (incubation at 37° C. in growth media). Cell attachment and spreading on the surfaces were analyzed and microscopic images were taken following several days of cell culture. The chondrocytes attached to the untreated surface and spread on the surface as expected. However, the chondrocytes remained un-attached to the treated surface and formed cell aggregates floating in the media. The treated surface remained free of cells after removing the media, demonstrating the ability of the treated surface for resisting chondrocyte attachment.

Experiments have been conducted relating to the formation of embryoid bodies from embryonic stem cells. The formation of embryoid bodies was successfully achieved using the 6-well polystyrene plates treated by the method of the subject invention. Untreated 6-well polystyrene plates were used as controls and embryoid bodies did not form due to the attachment of embryonic stem cells to the untreated surfaces during the long incubation time (up to 7 days). With the treated surfaces, attachment of the embryonic stem cells was generally avoided, and the embryonic stem cells remained in suspension during incubation. As such, without attachment, the embryonic stem cells generally avoided attachment-mediated differentiation, thereby permitting later enhanced embryoid body formation.

The subject invention may have applicability in various contexts. By way of non-limiting examples, the subject invention can be used to prepare polymeric surfaces to obtain the following advantages: maintaining cells in solution in suspended, unattached states; preventing stem cells from attachment-mediated differentiation; permitting enhanced formation of embryoid bodies from embryonic stem cells; preventing anchorage-dependent cells from dividing; reducing binding of serum proteins; and, enhancing signal-to-noise ratios in homogenous assays, such as Scintillation Proximity Assays.

What is claimed is:

1. A method for treating a polymeric surface to resist non-specific binding of biomolecules and attachment of cells, the method comprising:
   a) imparting a negative charge to the polymeric surface to produce a negatively-charged surface by disposing the polymeric surface into a substantially gas-free chamber, introducing a gas into the chamber, and exciting the gas to produce the negatively-charged surface;
   b) exposing the negatively-charged surface to a nitrogen-rich polymer to form a polymerized surface;
   c) exposing the polymerized surface to a first solution consisting of a first solvent and an oxidized polysaccharide in which pendant alcohol groups have been converted to aldehyde groups to form an aldehyde surface; and
   d) exposing the aldehyde surface to a second solution consisting of a second solvent and an amine-terminated polymer to form a Schiff base linkage therebetween, wherein the amine-terminated polymer forms an outer layer, and wherein the amine-terminated polymer is selected from the group consisting of amine-terminated hydrocarbyl polymers and amine-terminated polyethers, and then exposing the surface to a boron-based reducing agent.

2. The method of claim 1, wherein the amine-terminated polyether is amine-terminated polyethylene glycol.

3. The method of claim 1, wherein the exciting of the gas includes subjecting the gas to radiofrequency excitation.

4. The method of claim 1, wherein the gas is oxygen gas.

5. The method of claim 1, wherein the nitrogen-rich polymer is selected from the group consisting of: a polyalkylenimine and a polymeric amino acid.

6. The method of claim 5, wherein the nitrogen-rich polymer is selected from the group consisting of: polyethylenimine and poly-lysine.

7. The method of claim 1, wherein the oxidized polysaccharide is selected from the group consisting of: oxidized amylose, oxidized amylopectin, oxidized cellulose, oxidized chitin, oxidized guaran, oxidized glucomannan, and oxidized dextran.

8. The method of claim 1, wherein the polymeric surface is a polystyrene surface.

9. The method of claim 1, wherein the polymeric surface is a surface of a multiwell plate.

10. The method of claim 1, wherein the reducing agent is sodium borohydride.

11. The method of claim 1, wherein preparing the oxidized polysaccharide includes adding sodium m-periodate to a polysaccharide solution to produce an oxidizing solution.

12. The method of claim 11, wherein the preparing the oxidized polysaccharide further includes incubating the oxidizing solution.

13. The method of claim 12, wherein the incubating includes incubating the oxidizing solution at room temperature in the dark for four hours.

14. The method of claim 12, wherein the preparing the oxidized polysaccharide further includes removing the sodium m-periodate from the incubated oxidizing solution.

15. The method of claim 1, wherein first solvent is selected from the group consisting of water, a buffer, methanol, ethanol, and isopropanol.

16. The method of claim 1, wherein the nitrogen-rich polymer is poly-d-lysine.

17. The method of claim 1, wherein:
   the oxidized polysaccharide is oxidized dextran,
   the polymerized surface is exposed to the first solution for two hours,
   the amine-terminated polymer is amine-terminated polyethylene glycol, and
   the aldehyde surface is exposed to the second solution for one hour.

18. A surface treated by the method of claim 1.

19. The surface of claim 18, wherein the surface is the surface of a multiwell plate.

* * * * *